US010668236B2

(12) United States Patent
O'Connor et al.

(10) Patent No.: US 10,668,236 B2
(45) Date of Patent: Jun. 2, 2020

(54) ADAPTIVE PATIENT CIRCUIT COMPENSATION WITH PRESSURE SENSOR AT MASK APPARATUS

(71) Applicant: KONINKLIJKE PHILIPS N.V., Eindhoven (NL)

(72) Inventors: Nathan Francis O'Connor, Monroeville, PA (US); Christopher Scott Lucci, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1447 days.

(21) Appl. No.: 14/434,626

(22) PCT Filed: Oct. 10, 2013

(86) PCT No.: PCT/IB2013/059276
§ 371 (c)(1),
(2) Date: Apr. 9, 2015

(87) PCT Pub. No.: WO2014/057457
PCT Pub. Date: Apr. 17, 2014

(65) Prior Publication Data
US 2015/0265787 A1 Sep. 24, 2015

Related U.S. Application Data

(60) Provisional application No. 61/711,791, filed on Oct. 10, 2012.

(51) Int. Cl.
*A61M 16/00* (2006.01)
*A61M 16/06* (2006.01)
(Continued)

(52) U.S. Cl.
CPC .... *A61M 16/0051* (2013.01); *A61M 16/0003* (2014.02); *A61M 16/0069* (2014.02);
(Continued)

(58) Field of Classification Search
CPC .......... A61M 16/0051; A61M 16/0003; A61M 16/0069; A61M 16/026; A61M 16/06;
(Continued)

(56) References Cited

U.S. PATENT DOCUMENTS 6,431,171 B1  8/2002  Burton
7,845,350 B1  12/2010  Kayyali et al.
(Continued)

FOREIGN PATENT DOCUMENTS

EP  0651971 A1  5/1995
EP  2106818 A1  10/2009
(Continued)

OTHER PUBLICATIONS

Pressure Sensor for Sleep Apnea Mask, Silicon Microstructures Incorporated, Downloaded From http://www.si-micro.com/applications/medical/sleep-apnea, Mar. 7, 2012, 1 Page.

*Primary Examiner* — Timothy A Stanis
*Assistant Examiner* — Jonathan S Paciorek

(57) ABSTRACT

Systems and methods for providing respiratory therapy overcome various effects of transport delay within tubing of a respiratory therapy device by virtue of estimating and compensating for, e.g., a pressure drop in such tubing.

18 Claims, 3 Drawing Sheets

Figure 1:
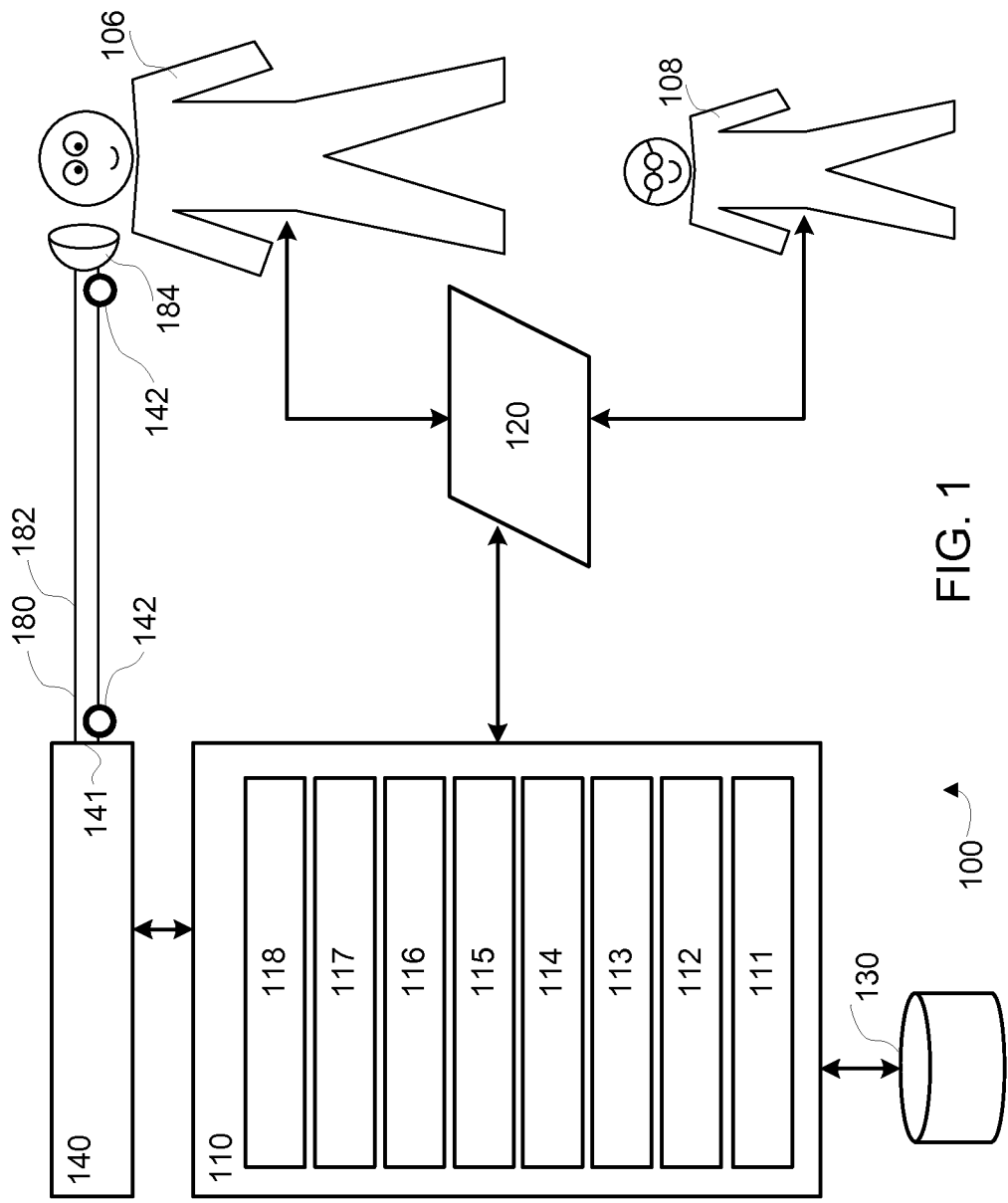

(51) Int. Cl.
*A61M 16/08* (2006.01)
*A61M 16/16* (2006.01)
*A61M 16/10* (2006.01)

(52) U.S. Cl.
CPC .......... *A61M 16/026* (2017.08); *A61M 16/06* (2013.01); *A61M 16/0875* (2013.01); *A61M 16/161* (2014.02); *A61M 2016/0027* (2013.01); *A61M 2016/0039* (2013.01); *A61M 2016/102* (2013.01); *A61M 2205/3303* (2013.01); *A61M 2205/3344* (2013.01); *A61M 2205/3365* (2013.01); *A61M 2205/3584* (2013.01); *A61M 2205/3592* (2013.01); *A61M 2205/50* (2013.01); *A61M 2205/505* (2013.01); *A61M 2205/52* (2013.01)

(58) Field of Classification Search
CPC ............ A61M 16/161; A61M 16/0875; A61M 2016/0027; A61M 2016/0039; A61M 2016/10; A61M 2016/00272; A61M 2205/3303; A61M 2205/3344; A61M 2205/3365; A61M 2205/3584; A61M 2205/3592
See application file for complete search history.

(56) References Cited

U.S. PATENT DOCUMENTS

| | | | |
|---|---|---|---|
| 2001/0004893 A1* | 6/2001 | Biondi | A61M 16/00 128/204.18 |
| 2002/0088465 A1* | 7/2002 | Hill | A61M 16/00 128/204.23 |
| 2004/0211423 A1* | 10/2004 | Baecke | A61M 16/024 128/204.23 |
| 2005/0241640 A1 | 11/2005 | Baecke et al. | |
| 2006/0162728 A1 | 7/2006 | Delache et al. | |
| 2007/0163590 A1* | 7/2007 | Bassin | A61M 16/00 128/204.23 |
| 2009/0293876 A1 | 12/2009 | Soliman et al. | |
| 2011/0146681 A1 | 6/2011 | Jafari et al. | |
| 2011/0308518 A1 | 12/2011 | Mc Groary et al. | |

FOREIGN PATENT DOCUMENTS

| | | |
|---|---|---|
| WO | 0220076 A2 | 3/2002 |
| WO | 2007045036 A1 | 4/2007 |
| WO | 2011054038 A1 | 5/2011 |
| WO | 2011141845 A1 | 11/2011 |
| WO | 2012156885 A1 | 11/2012 |

* cited by examiner

ADAPTIVE PATIENT CIRCUIT COMPENSATION WITH PRESSURE SENSOR AT MASK APPARATUS

CROSS-REFERENCE TO PRIOR APPLICATIONS

This application is the U.S. National Phase application under 35 U.S.C. § 371 of International Application No. PCT/IB2013/059276, filed on Oct. 10, 2013, which claims the benefit of U.S. Provisional Patent Application No. 61/711,791, filed on Oct. 10, 2012. These applications are hereby incorporated by reference herein.

The present disclosure pertains to a system and method for providing respiratory therapy through a pressure support device, and, in particular, to modeling, estimating, and compensating for one or more effects of transport delay through tubing within the pressure support device, including but not limited to a pressure drop between the output of a pressure generator and the point of delivery of a pressurized flow of breathable gas.

It is well known that some types of respiratory therapy involve the delivery of a flow of breathable gas to the airway of a subject. It is known that a flow of breathable gas may be pressurized at varying levels of pressure, even during a single therapy session. It is known that one or more algorithms may operate to control and/or adjust the pressure level or flow used in respiratory therapy. It is known that measurements or estimations of various gas parameters can be used in a feedback or feedforward manner to control and/or adjust the pressure level used in respiratory therapy. It is known that there are practical limitations to the responsiveness and/or stability of a respiratory therapy device, due, in part, to the transport delay of a pressure wave propagating through the respiratory therapy device on its way to the point of delivery, such as the tubing and mask of a patient.

Accordingly, it is an object of one or more embodiments of the present invention to provide a system for providing respiratory therapy during a therapy session to a subject having an airway. The system comprises a pressure generator, a subject interface, one or more sensors, and one or more processors. The pressure generator is configured to generate a pressurized flow of breathable gas for delivery to the airway of the subject. The pressure generator has an output configured to expel the pressurized flow of breathable gas. The subject interface is configured to guide the pressurized flow of breathable gas from the output of the pressure generator to a point of delivery at or near the airway of the subject. The subject interface causes a pressure drop between the output of the pressure generator and the point of delivery during delivery of the pressurized flow of breathable gas. The one or more sensors are configured to generate output signals conveying information related to one or more gas parameters of the pressurized flow of breathable gas. The output signals are generated in an ongoing manner during the therapy session. One of the one or more sensors is disposed at or near the point of delivery and/or at or near the output of the pressure generator. The one or more processors are configured to execute processing modules.

The processing modules include an estimation module, a target module, a control module, and/or other modules. The estimation module is configured to estimate the pressure drop between the output of the pressure generator and the point of delivery during delivery of the pressurized flow of breathable gas based on the generated output signals. The estimation by the estimation module is performed in an ongoing manner during the therapy session. The target module is configured to determine a target pressure for the pressurized flow of breathable gas that compensates for the estimated pressure drop. The target pressure is in accordance with a therapy regimen. The control module is configured to adjust levels of one or more gas parameters of the pressurized flow of breathable gas based on the determined target pressure.

It is yet another aspect of one or more embodiments of the present invention to provide a method for providing respiratory therapy during a therapy session to a subject having an airway implemented in a system including a pressure generator, a subject interface, and one or more sensors. The method comprises generating a pressurized flow of breathable gas for delivery to the airway of the subject via an output of the pressure generator; guiding the pressurized flow of breathable gas from the output of the pressure generator to a point of delivery at or near the airway of the subject via the subject interface, wherein the subject interface causes a pressure drop between the output of the pressure generator and the point of delivery during delivery of the pressurized flow of breathable gas; generating output signals conveying information related to one or more gas parameters of the pressurized flow of breathable gas, wherein the output signals are generated in an ongoing manner during the therapy session; estimating the pressure drop between the output of the pressure generator and the point of delivery of the pressurized flow of breathable gas based on the generated output signals, wherein the estimation is performed in an ongoing manner during the therapy session; determining a target pressure for the pressurized flow of breathable gas that compensates for the estimated pressure drop, wherein the target pressure is in accordance with a therapy regimen; and adjusting levels of one or more gas parameters of the pressurized flow of breathable gas based on the determined target pressure.

It is yet another aspect of one or more embodiments to provide a system configured providing respiratory therapy during a therapy session to a subject. The system comprises pressure means, guiding means, means for estimating a pressure drop, means for determining a target pressure, and means for adjusting levels of one or more gas parameters. The pressure means is for generating a pressurized flow of breathable gas for delivery to the airway of the subject. The guiding means is for guiding the pressurized flow of breathable gas from an output of the pressure means to a point of delivery at or near the airway of the subject. The guiding means causes a pressure drop between the output of the pressure means and the point of delivery during delivery of the pressurized flow of breathable gas. The means for generating output signals conveys information related to one or more gas parameters of the pressurized flow of breathable gas. The output signals are generated in an ongoing manner during the therapy session. Operation of the means for estimating the pressure drop between the output of the pressure means and the point of delivery of the pressurized flow of breathable gas is based on the generated output signals. Operation of the means for estimating is performed in an ongoing manner during the therapy session. The means for determining a target pressure for the pressurized flow of breathable gas compensates for the estimated pressure drop. The target pressure is in accordance with a therapy regimen. Operation of the means for adjusting levels of one or more gas parameters of the pressurized flow of breathable gas is based on the determined target pressure.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 2:
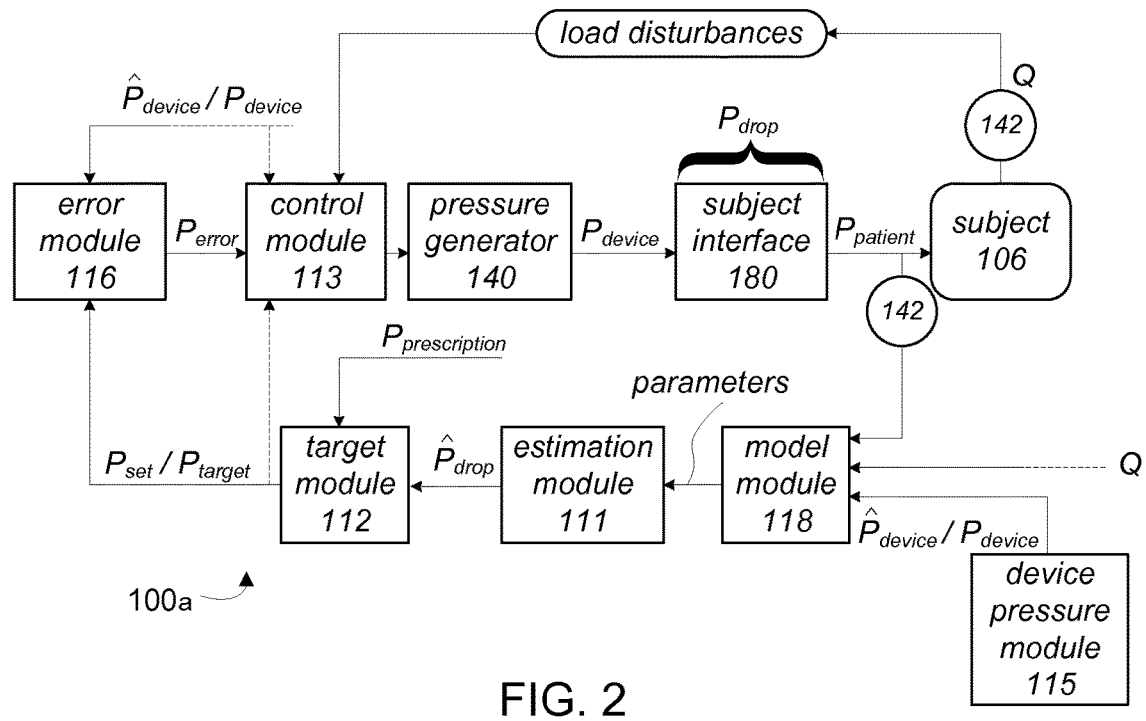
Figure 3:
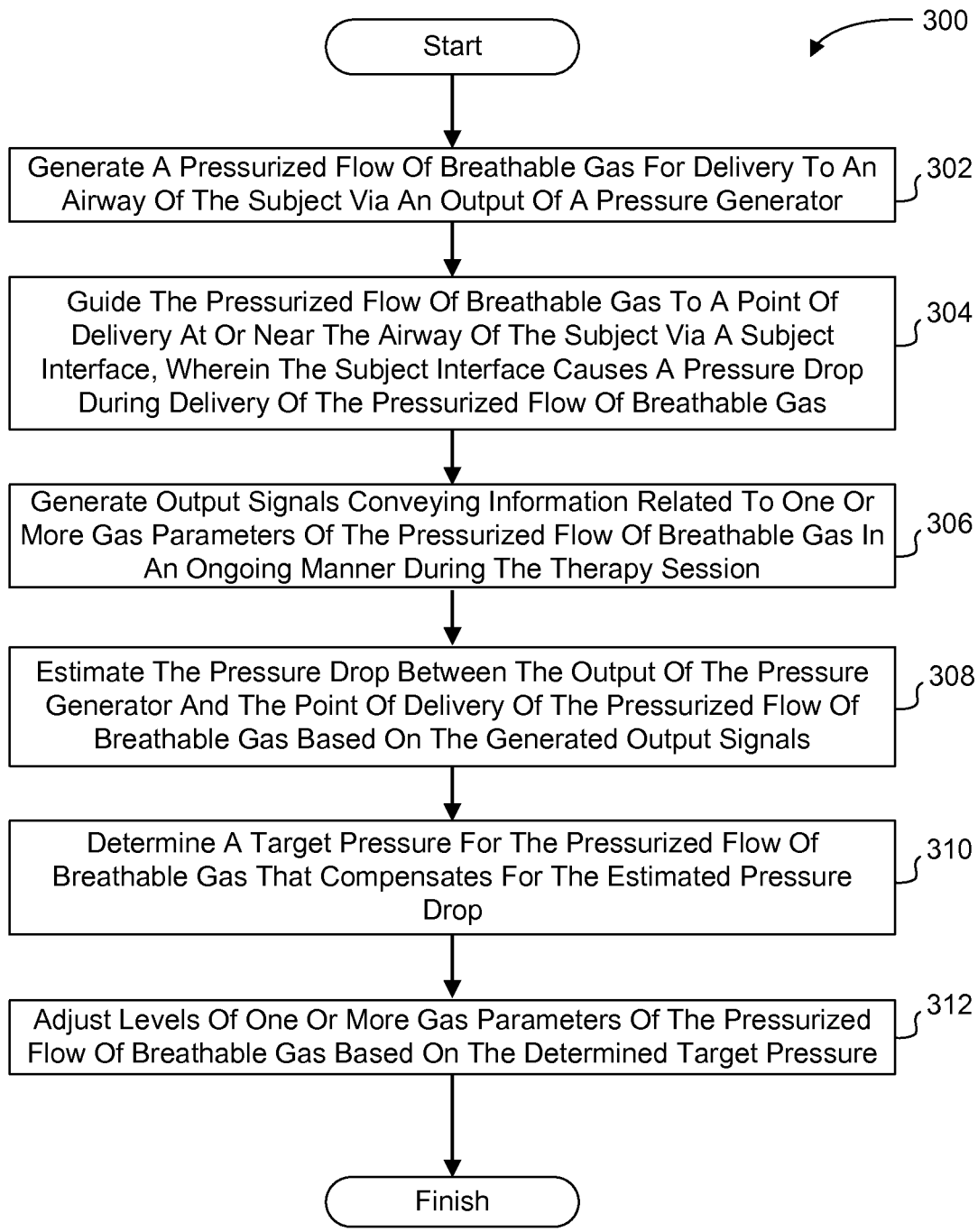

FIG. 1 schematically illustrates a system for providing respiratory therapy to a subject in accordance with one or more embodiments;

FIG. 2 schematically illustrates an exemplary system for providing respiratory therapy to a subject;

FIG. 3 illustrates a method for providing respiratory therapy to a subject; and

Figure 4:
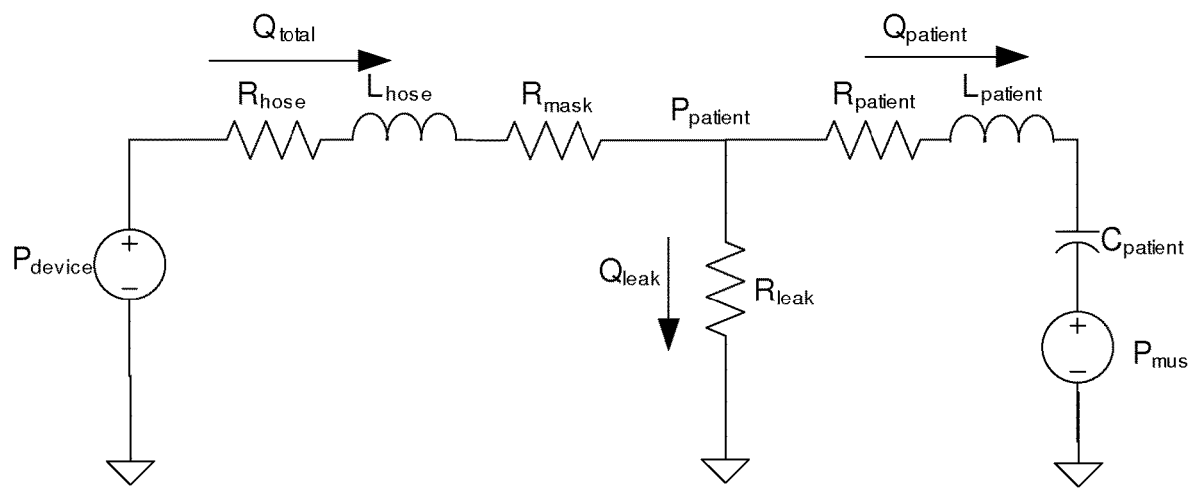

FIG. 4 schematically illustrates an electrical circuit representation of a system for providing respiratory therapy to a subject in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 for providing respiratory therapy to a subject 106. System 100 may be implemented as, integrated with, and/or operating in conjunction with a respiratory therapy device. System 100 dynamically models, measures, determines, and/or estimates one or more effects of transport delay through tubing and/or other pneumatic system parameters within a respiratory therapy device, including but not limited to a pressure drop dynamically during a therapy session and compensates for one or more effects in order to improve the quality, responsiveness, and/or stability of the respiratory therapy device and/or the provided respiratory therapy.

Quality of a respiratory therapy device and/or the provided respiratory therapy may pertain to the precision of the level and/or timing of one or more gas parameters of a delivered pressurized flow of breathable gas, in particular in response to load-side disturbances such as flow changes from the subject and/or components of system 100. Alternatively, and/or simultaneously, quality may pertain to the bandwidth of the respiratory therapy device. Alternatively, and/or simultaneously, quality may pertain to the amount of noise or the signal-to-noise ratio within a respiratory therapy device. Responsiveness of a respiratory therapy device may pertain to how well and/or how rapidly the device handles load disturbances (and/or other flow changes) and/or setpoint changes within the system. Such changes may include, without limitation, breathing, sneezing, coughing and/or other actions by subject 106, as well as changes due to hardware components, such as a tube moving, bending, etc. In some cases, responsiveness may be characterized by a response rate. Stability of a respiratory therapy device may pertain to the likelihood of introducing oscillations within the device during a therapy session. Alternatively, and/or simultaneously, stability may be characterized by a gain margin and a phase margin.

A therapy "session" of using system 100 may be defined as a period of substantially uninterrupted therapeutic usage of system 100, not to exceed some upper threshold of (consecutive) hours. The upper threshold may be, for example, about 6 hours, about 8 hours, about 10 hours, about 12 hours, about 16 hours, about 24 hours and/or other time periods. If the respiratory therapy is used to treat sleeping disorders the related session length may correspond to the sleeping pattern of a subject. A typical session length may thus be about eight hours. Alternatively, and/or simultaneously, a therapy session may be defined as a period of substantially uninterrupted therapeutic usage of system 100, not to span less than some lower threshold of (consecutive) units of time, and/or at least a minimum period of time apart from a previous session. The lower threshold may be, for example, about 15 minutes, about 30 minutes, about 1 hour, about 2 hours, about 3 hours, about 4 hours, about 5 hours and/or other time periods. For example, a minute of usage may be too short to be regarded as a session. For example, two 3-hour periods of usage separated by a 10-minute gap may be regarded as one session rather than two sessions. Individual therapy sessions may have a beginning and an end.

In some embodiments, one or more operative levels (e.g. pressure, volume, etc.) are adjusted on a relatively ongoing manner (e.g., between individual breaths, every few breaths, every few seconds, every minute, etc.) during an individual therapy session to titrate the therapy and/or to compensate for other changes in the patient circuit.

System 100 includes one or more of a pressure generator 140, a delivery circuit 180, one or more sensors 142, an electronic storage 130, a user interface 120, a processor 110, an estimation module 111, a target module 112, a control module 113, a patient pressure module 114, a device pressure module 115, an error module 116, a parameter determination module 117, and/or other components.

Pressure generator 140 of system 100 in FIG. 1 may be integrated, combined, coupled, and/or connected with a (positive) airway pressure device (PAP/CPAP/BiPAP®/ etc.). Pressure generator 140 may be configured to provide a pressurized flow of breathable gas for delivery to the airway of subject 106, e.g. via an output 141 of pressure generator 140, and/or via a delivery circuit 180. Delivery circuit 180 may sometimes be referred to as subject interface 180. Subject 106 may initiate one or more phases of respiration. Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas. In addition to alternating between multiple levels, the inhalation pressure level may ramp up or down according to a predetermined slope (absolute and/or relative, e.g. dependent on breathing rate) for any specified section of a phase. Similar features may be available for exhalation phases. The pressure levels may be either predetermined and fixed, follow a predetermined dynamic characteristic, or they may dynamically change breath-to-breath or night-to-night depending on sensed breathing, breathing disorder, or other physiological characteristics. Pressure generator 140 is configured to adjust one or more of pressure levels, flow, humidity, velocity, acceleration, and/or other parameters of the pressurized flow of breathable gas, e.g. in substantial synchronization with the breathing cycle of the subject.

An airway pressure device may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. System 100 may be configured to provide types of therapy including types of therapy where a subject performs inspiration and/or expiration of his own accord or where the device provides negative airway pressure.

The functional relation between the pressure level at output 141 of pressure generator 140 and the pressure level at the point of delivery to subject 106 may be referred to as a transfer function. A parameter-based model that models one or more of subject interface 180, interaction between subject interface 180 and subject 106, and/or other components within system 100 may be used to analyze the transfer function in the context of a closed-loop feedback/feedforward system. The parameter-based model may contain a patient model as well as a patient interface circuit pneumatic model. The parameter-based model may be dynamic, e.g. the parameters may change in value dynamically, or model elements may be added, removed, and/or reconfigured dynamically to better estimate the patient model or patient interface circuit pneumatic model. Usage and/or analysis of the parameter-based model, e.g. pertaining to the transfer function, may pertain to the effects of a time delay, such as the transport delay of a pressure wave propagating through subject interface 180, on, e.g., system responsiveness and stability. An example of a transfer function for an input $X_{set}$ versus an output $X_{Actual}$ is given by the equation below:

$$\frac{X_{Actual}}{X_{Set}} = \frac{KG(s)}{1 + KG(s)} = \frac{K}{s^2 + 2s^2 + s + K},$$

for a gain K

Note that a time delay in may contribute a linearly increasing phase lag in which the degree of negative phase contribution is proportional to frequency. Adding a small time delay may affect only the phase, thereby decreasing the stability margins. If the time delay is large enough, a reduction in gain may be needed to maintain stability and/or limit other undesirable effects, effectively limiting the response speed.

A pressurized flow of breathable gas is delivered from pressure generator 140 to the airway of subject 106 via delivery circuit 180. Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas is communicated between subject interface appliance 184 and pressure generator 140. Conduit 182 may comprise a standard 22 mm diameter hose (other common diameters range between ¾" and 1") or, in certain embodiments, a much smaller diameter hose that is in the range of ⅓ of a standard size hose. Such a hose, which may be referred to as a restricted flow hose or limited flow hose, (for example, having a diameter ranging between ¼" and ⅓", or alternatively between 6 mm and 9 mm) may have a greater resistance to gas flow and/or may be smaller and/or less obtrusive.

Subject interface appliance 184 of system 100 in FIG. 1 is configured to deliver the pressurized flow of breathable gas to the airway of subject 106. As such, subject interface appliance 184 may include any appliance suitable for this function. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, FRAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store timing information (including duration of inhalation phases and exhalation phases as well as transitional moments), one or more (breathing) parameters and/or other parameters (as discussed elsewhere herein), pressure levels, pressure drop estimated at various moments, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, information indicating adequacy of treatment, and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing occurrences of respiratory events throughout a period during which the subject is receiving therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying measurements related to gas parameters of respiratory airflow, parameters related to airway mechanics, and/or other parameters. Gas parameters may include flow, (airway) pressure, humidity, velocity, acceleration, and/or other gas parameters. Output signals may convey measurements related to respiratory parameters. Sensor 142 may be in fluid communication with conduit 182 and/or subject interface appliance 184. Sensor 142 may generate output signals related to physiological parameters pertaining to subject 106. Parameters may be associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement and/or unit that may serve as a proxy for any of the parameters listed herein through a previously known and/or calibrated mathematical relationship. Sensed signals may include any information obtained by or extracted from fundamental relationships involving control parameters or surrogates.

The illustration of sensor 142 including two members in FIG. 1 is not intended to be limiting. In some hardware configurations, system 100 may use only one sensor 142. The individual sensor 142 may be located at or near subject interface appliance 184, or at other locations. In some hardware configurations, system may include a sensor 142 at or near output 141 of pressure generator 140. The illustration of a sensor 142 at or near subject interface appliance 184 and a sensor 142 at or near output 141 of pressure generator 140 is not intended to be limiting. Resulting signals or information from one or more sensors 142 may be transmitted to processor 110, user interface 120, electronic storage 130, and/or other components of system 100. This transmission may be wired and/or wireless.

The one or more sensors 142 may be configured to generate output signals in an ongoing manner during a therapy session. This may include generating signals intermittently, periodically (e.g. at a sampling rate), continuously, continually, at varying intervals, and/or in other ways that are ongoing during at least a portion of the therapy session. For example, in some embodiments, the generated output signals may be considered as a vector of output signals, such that a vector includes multiple samples of information conveyed related to one or more gas parameters and/or other parameters. Different parameters may be related to different vectors. A particular parameter determined in an ongoing manner from a vector of output signals may be considered as a vector of that particular parameter.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of estimation module 111, target module 112, control module 113, patient pressure module 114, device pressure module 115, error module 116, parameter determination module 117, model module 118, and/or other modules. Processor 110 may be configured to execute modules 111-118 by software; hardware; firmware; some combination of software, hardware, and/or firmware; and/or other mechanisms for configuring processing capabilities on processor 110.

It should be appreciated that although modules 111-118 are illustrated in FIG. 1 as being co-located within a single processing unit, in embodiments in which processor 110 includes multiple processing units, one or more of modules 111-118 may be located remotely from the other modules. The description of the functionality provided by the different modules 111-118 described herein is for illustrative purposes, and is not intended to be limiting, as any of modules 111-118 may provide more or less functionality than is described. For example, one or more of modules 111-118 may be eliminated, and some or all of its functionality may be incorporated, shared, integrated into, and/or otherwise provided by other ones of modules 111-118. Note that processor 110 may be configured to execute one or more additional modules that may perform some or all of the functionality attributed below to one of modules 111-118.

Parameter determination module 117 of system 100 in FIG. 1 is configured to determine one or more gas parameters, breathing parameters, and/or other parameters based on one or more of output signals generated by sensor(s) 142 and/or other information sources. Determinations may be based on measurements, calculations, estimations, approximations, previously known and/or calibrated mathematical relationships, and/or other ways to determine a parameter. The other information sources may include motor currents, motor voltage, motor parameters, valve parameters, and/or other sources. The determined parameters may include system parameters and/or controlled parameters, i.e. not just sensed signals.

Operation of parameter determination module 117 may be performed in an ongoing manner. The one or more gas parameter may include and/or be related to one or more of (peak) flow rate, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more gas parameters may be determined at different locations and/or positions within system 100, including within pressure generator 140, at or near output 141 of pressure generator 140, within subject interface 180, at or near the point of engagement between pressure generator 140 and subject interface 180, within conduit 182, at or near an input of conduit 182, at or near an output of conduit 182, within subject interface appliance 184, at or near an input of subject interface appliance 184, at or near an output of subject interface appliance 184, and/or at other locations and/or positions within system 100.

Parameter determination module 117 may derive one or more breathing parameters from one or more determined gas parameters and/or generated output signals. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters.

Parameter determination module 117 may derive vectors of parameters in an ongoing manner during a therapy session from vectors of generated output signals and/or other (vectors of) determined parameters.

Model module 118 is configured to dynamically manage a parameter-based system model that models one or more of subject interface 180, interaction between subject interface 180 and subject 106, subject 106, and/or other components within system 100. The parameter-based model may be derived using electrical circuit representation of system 100. The parameter-based model includes one or more model parameters related to one or more of pneumatic impedance, resistance, inertance/inductance, capacitance, and/or other characteristics. The parameter-based model may separately represent resistive, compliance, inertance, and/or other (pneumatic) components of the patient pneumatic model. Model module 118 may be configured to adjust one or more model parameters described herein in an ongoing manner during a therapy session. As used herein, "adjusting" a model parameter may include correcting a model parameter. Adjustments by model module 118 may be based on one or more of information from parameter determination module 117 and/or the output signals generated by one or more sensors 142.

By way of illustration, FIG. 4 schematically illustrates model 100b, an electrical circuit representation of system 100 as shown in FIG. 1. Note that in FIG. 4 "hose" may refer to conduit 182 as shown in FIG. 1, or subject interface 180 as shown in FIG. 1, without subject interface appliance 184 as shown in FIG. 1. Note that in FIG. 4 "mask" refers to subject interface appliance 184 as shown in FIG. 1. As depicted in FIG. 4, $P_{device}$ is the pressure level at the output of the pressure generator, $R_{hose}$ is the "hose" resistance, $L_{hose}$, is the "hose" inertance, $R_{mask}$ is the resistance of the subject interface appliance, $P_{patient}$ is the patient pressure or subject pressure, $R_{leak}$ is the leak resistance, $R_{patient}$ is the resistance of the patient airways and lungs, $L_{patient}$, is inertance of the patient airways, $C_{patient}$ is the compliance of the patient airway and lungs, $P_{mus}$ is the is pressure generated by the patient diaphragm, $Q_{total}$ is the total flow measured by the device, $Q_{leak}$ is the leak flow, and $Q_{patient}$ is the patient flow. Variations of model 100b in patient which inertance and/or compliance subject interface appliance 184 are included are contemplated within the scope of this disclosure.

Through circuit analysis of model 100b in FIG. 4, the following equations representing relations within the system may be derived:

$$P_{device} - P_{patient} = R_{hose} \cdot Q + L_{hose} \cdot \frac{dQ}{dt} + R_{mask} \cdot Q$$

$$P_{device} - P_{patient} = (R_{hose} + R_{mask}) \cdot Q + L_{hose} \cdot \frac{dQ}{dt}$$

$$R_{circuit} = R_{hose} + R_{mask}$$

$$P_{device} - P_{patient} = R_{circuit} \cdot Q + L_{hose} \cdot \frac{dQ}{dt}$$

Additional specificity using a more detailed or more complex parameter-based model is contemplated and would be implemented in these equations by additional terms. In some embodiments, these equations may be solved using a least-squared error solution:

$$[Q \ \dot{Q}]^T [Q \ \dot{Q}] \begin{bmatrix} R_{circuit} \\ L_{hose} \end{bmatrix} = [Q \ \dot{Q}]^T [P_{device} - P_{patient}]$$

$$\begin{bmatrix} \sum_{n=1}^{N} Q[n]^2 & \sum_{n=1}^{N} Q[n] \cdot \dot{Q}[n] \\ \sum_{n=1}^{N} \dot{Q}[n]^2 & \sum_{n=1}^{N} \dot{Q}[n] \cdot Q[n] \end{bmatrix} \begin{bmatrix} R_{circuit} \\ L_{hose} \end{bmatrix} = [Q \ \dot{Q}]^T [P_{device} - P_{patient}]$$

$$\begin{bmatrix} R_{circuit} \\ L_{hose} \end{bmatrix} = \begin{bmatrix} \sum_{n=0}^{N} Q[n]^2 & \sum_{n=0}^{N} Q[n] \cdot \dot{Q}[n] \\ \sum_{n=0}^{N} \dot{Q}[n]^2 & \sum_{n=0}^{N} \dot{Q}[n] \cdot Q[n] \end{bmatrix}^{-1} [Q \ \dot{Q}]^T [P_{device} - P_{patient}]$$

In some embodiments, other solutions (and/or other data fitting techniques) may be implemented and/or contemplated that may be used to determine and/or estimate one or more model parameters of the parameter-based model, such as, e.g., $R_{circuit}$ and $L_{hose}$, based on one or more output signals generated by one or more sensors 142 as depicted in FIG. 1.

Estimation module 111 is configured to estimate a pressure drop over at least part of subject interface 180. For example, the estimated pressure drop may be between output 141 of pressure generator 140 (and/or a point near output 141) and the point of delivery of the pressurized flow of breathable gas (and/or a point near the point of delivery) during delivery of the pressurized flow of breathable gas. Pressure drop may be related to pneumatic impedance of subject interface 180 and/or other components of system 100. In some embodiments, estimations by estimation module 111 may be based on one or more model parameters of the parameter-based model of model module 111, such that adjustments of the one or more model parameters of the parameter-based model are dynamically reflected in corresponding adjustments by estimation module 111.

Pressure drop may vary with differences in hose length (e.g. the length of conduit 182), conduit diameter, bends in a hose or tube, and/or other factors, including dynamic factors that change during a therapy session. Estimation by estimation module 111 may be based on the generated output signals. Estimation by estimation module 111 may be performed in an ongoing manner during a therapy session. Alternatively, and/or simultaneously, estimations by estimation module 111 may be triggered when a particular error within system 100 breaches a predetermined threshold. For example, when the difference between a particular measured parameter is greater than an estimation of the same parameter, this occurrence may trigger operations from one or more modules within system 100.

In some embodiments, the estimated pressure drop $\hat{P}_{drop}$ may be based on a function (e.g. a differential function) of the flow Q measured within subject interface 180 and/or elsewhere in the patient circuit, the pressure $P_{patient}$ measured at or near the point of delivery of the pressurized flow of breathable gas, the pressure measured or estimated at or near output 141 of pressure generator 140, and/or other information. The function may use current and past samples of the listed (vectors of) parameters.

In some embodiments, the functions used may be based on a particular model used to represent system 100 during use. Examples include electrical circuit representations of the pneumatic characteristics of system 100. Through circuit analysis, the relations between, e.g., patient pressure and device pressure may be represented as differential equations that may be solved in various ways, including by way of a least-squared error solution. Other patient circuit models are contemplated, as well as other data fitting techniques to solve such models.

If one of the one or more sensors 142 is located at or near output 141, the estimated pressure drop may be based on a measured pressure at or near output 141 referred to as $P_{device}$ or device pressure. Alternatively, and/or simultaneously, the estimated pressure drop may be based on an estimated pressure at or near output 141 referred to as $\hat{P}_{device}$. Such an estimated pressure may e.g. be based on flow Q and a priori information including, but limited to, blower speed, valve drive current, and/or any other mechanical unit of measurement of a component of pressure generator 140 or of a device that pressure generator 140 is integrated, combined, or connected with, and/or a proxy of such a measurement.

In other words, when using $\hat{P}_{device}$:

$\hat{P}_{drop}[k] = f(\vec{P}_{patient}, \vec{Q}, \vec{\hat{P}}_{device})$, for the $k^{th}$ sample in a vector Target module 112 is configured to determine a target pressure $P_{target}$ for the pressurized flow of breathable gas that compensates for the estimated pressure drop. The target pressure may interchangeably be referred to as $P_{set}$. The target pressure may be in accordance with a therapy regimen, and may dynamically change and/or titrate during one or more therapy sessions. For example, the therapy regimen may prescribe a particular pressure referred to as $P_{prescription}$. Determination by target module 112 may be performed in an ongoing manner during the therapy session. The target pressure may be adjusted as either the prescribed pressure and/or the estimated pressure drop change.

In other words (and by way of non-limiting example):

$P_{set}[k] = P_{prescription}[k] + \hat{P}_{drop}[k]$, for the $k^{th}$ sample in a vector Control module 113 is configured to control operation of system 100 during a therapy session. Control module 113 may be configured to control the pressure generator to adjust one or more levels of gas parameters of the pressurized flow of breathable gas in accordance with one or more of a (respiratory) therapy regimen, based on target pressures determined by target module 112, based on one or more algorithms that control adjustments and/or changes in the pressurized flow of breathable gas, and/or based on other factors. Control module 113 may be configured to control pressure generator 140 to provide the pressurized flow of breathable gas. Control module 113 may be configured to control pressure generator 140 such that one or more gas parameters of the pressurized flow of breathable gas are varied over time in accordance with a respiratory therapy regimen.

Parameters determined by parameter determination module 117, and/or received through sensors 142 may be used by control module 113 and/or other modules, e.g. in a feedback manner, to adjust one or more therapy modes/settings/operations of system 100. Alternatively, and/or simultaneously, signals and/or information received through user interface 120 may be used by control module 113 and/or other modules, e.g. in a feedback manner, to adjust one or more therapy modes/settings/operations of system 100. Control module 113 may be configured to time its operations relative to transitional moments in the breathing cycle of a subject, over multiple breath cycles, and/or in any other timing relation. For example, estimation module 111 may be configured to estimate the pressure drop based, at least in part, on a flow rate within subject interface 180 as determined by parameter determination module 117.

Some respiratory therapy devices that measure $P_{patient}$ may determine a pressure error $P_{error}$ (commonly to be used in a feedback manner to adjust the pressure level of a pressurized flow of breathable gas) based on the difference between either $P_{prescription}$ or $P_{target}$ and $P_{patient}$. Some respiratory therapy devices that measure $P_{device}$ may determine a pressure error $P_{error}$ based on the difference between either $P_{prescription}$ or $P_{target}$ and $P_{device}$. In either of these cases the quality, stability, and/or responsiveness of the respiratory therapy device may be negatively and/or non-negligibly affected by the transport delay of a pressure wave propagating through the subject interface (and/or any other tube or component of these respiratory therapy devices). By way of non-limiting example, transport delay may contribute to (linearly increasing) phase lag, and/or a reduced gain margin.

System 100 accounts and/or compensates for all or most of the negative effects of such transport delay by virtue of, in part, basing adjustments by control module 113 on the estimated and/or measured pressure at or near output 141 of pressure generator 140.

Error module 116 is configured to determine a pressure error $P_{error}$ based on a difference between (and/or other mathematical operations involving) the target pressure $P_{set}$ (as e.g. determined by target module 112) and the measured pressure ($P_{device}$) or estimated pressure ($\hat{P}_{device}$) at or near output 141 of pressure generator 140 (as e.g. determined by parameter determination module 117 and/or device pressure module 115). The pressure error may be determined in an ongoing manner during (at least part of) a therapy session. For example, a vector of the pressure error may be updated intermittently using samples of generate output signals, estimated pressure drop, and/or other (vectors of) parameters or information such that subsequent determinations of the pressure error are less than about 1 second apart, less than about 10 seconds apart, less than about 30 seconds apart, less than about 1 minute apart, less than about 10 minutes apart, and/or less than other time periods apart. The pressure error may subsequently be used elsewhere in system 100, for example by control module 113, e.g. in a feedback manner, to adjust levels of one or more gas parameters of the pressurized flow of breathable gas.

In other words (and by way of non-limiting example using the estimated device pressure):

$$P_{error}[k] = P_{set}[k-1] - \hat{P}_{device}[k-1], \text{ for the } k^{th} \text{ sample in a vector}$$

Rapid, ongoing, adaptive, and/or dynamic determination of pressure drop during a therapy session facilitates both improved quality, stability, and/or responsiveness of system 100, as well as the ability for a patient to test more interface equipment in a shorter amount of time.

Patient pressure module 114 is configured to determine patient pressure $P_{patient}$ at or near the point of delivery of the pressurized flow of breathable gas to the airway of subject 106. Determination by patient pressure module 114 may be based on the generated output signals from one or more sensors 142, in particular a sensor 142 located at or near the point of delivery, e.g. in subject interface appliance 184.

Device pressure module 115 is configured to determine a device pressure at or near output 141 of pressure generator 140. Determination may be based on measurements and/or estimations. If one of the one or more sensors 142 is located at or near output 141, determination by device pressure module 115 may be based on the pressure module 115 may be based on an estimated pressure $\hat{P}_{device}$. Such an estimated pressure may e.g. be based on flow Q and a priori information including, but limited to, blower speed, valve drive current, and/or any other mechanical unit of measurement of a component of pressure generator 140 or of a device that pressure generator 140 is integrated, combined, or connected with, and/or a proxy of such a measurement.

By way of illustration, FIG. 2 schematically illustrates an exemplary system 100a for providing respiratory therapy to a subject in substantially the same or similar manner as system 100 of FIG. 1. Referring to FIG. 2, pressure generator 140 provides a pressurized flow of breathable gas, having a pressure of $P_{device}$, to subject interface 180. The output of subject interface 180 is in fluid communication with subject 106, such that the provided pressure is $P_{patient}$. The difference between $P_{device}$ and $P_{patient}$ is the pressure drop $P_{drop}$. Through a sensor 142 depicted above subject 106, a flow Q may be measured. Load disturbances within system 100a may be fed back, by way of non-limiting example to control module 113 as depicted, such that the operation of pressure generator 140 may be adjusted to compensate for load disturbances. Control of pressure generator may be performed by control module 113. Through a sensor 142 depicted below subject 106, patient pressure $P_{patient}$ may be determined. The pressure drop $\hat{P}_{drop}$ may be estimated by estimation module 111 based on the patient pressure, flow Q (as determined by a sensor 142 depicted above subject 106), and one or both of measured device pressure $P_{device}$ and/or estimated device pressure $\hat{P}_{device}$, depending on the hardware configuration used for system 100a. The device pressure may be determined by device pressure module 115. Target module 112 may determine pressure target $P_{target}$ (also referred to as $P_{set}$) based on prescription pressure $P_{prescription}$ and the estimated pressure drop. Error module 116 may determine pressure error $P_{error}$ based on the target pressure from target module 112 and one or both of measured device pressure $P_{device}$ and/or estimated device pressure $\hat{P}_{device}$. Pressure error $P_{error}$, target pressure $P_{target}$, and/or the device pressure may be used by control module 113, in addition to information about flow Q and/or the load disturbances, to control pressure generator 140. Note that system 100a and its depicted components and interconnections in FIG. 2 are merely exemplary, and not intended to be limiting in any way.

FIG. 3 illustrates a method 300 for providing respiratory therapy to a subject. The operations of method 300 presented below are intended to be illustrative. In certain embodiments, method 300 may be accomplished with one or more additional operations not described, and/or without one or more of the operations discussed. Additionally, the order in which the operations of method 300 are illustrated in FIG. 3 and described below is not intended to be limiting.

In certain embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow of breathable gas is generated for delivery to the airway of the subject via an output of the pressure generator. In some embodiments, operation 302 is performed by a pressure generator similar to or substantially the same as pressure generator 140 (shown in FIG. 1 and described herein).

At an operation 304, the pressurized flow of breathable gas is guided from the output of the pressure generator to a point of delivery at or near the airway of the subject via a subject interface. The subject interface causes a pressure drop between the output of the pressure generator and the point of delivery during delivery of the pressurized flow of breathable gas. In some embodiments, operation 304 is performed by a subject interface the same as or similar to subject interface 180 (shown in FIG. 1 and described herein).

At an operation 306, output signals conveying information related to one or more gas parameters of the pressurized flow of breathable gas are generated. The output signals are generated in an ongoing manner during the therapy session. In some embodiments, operation 306 is performed by one or more sensors the same as or similar to sensors 142 (shown in FIG. 1 and described herein).

At an operation 308, the pressure drop between the output of the pressure generator and the point of delivery of the pressurized flow of breathable gas is estimated based on the generated output signals. The estimation is performed in an ongoing manner during the therapy session. In some embodiments, operation 308 is performed by an estimation module the same as or similar to estimation module 111 (shown in FIG. 1 and described herein).

At an operation 310, a target pressure for the pressurized flow of breathable gas is determined that compensates for the estimated pressure drop. The target pressure is in accordance with a therapy regimen. The determination is performed in an ongoing manner during the therapy session. In some embodiments, operation 310 is performed by a target module the same as or similar to target module 112 (shown in FIG. 1 and described herein).

At an operation 312, levels of one or more gas parameters of the pressurized flow of breathable gas are adjusted based on the determined target pressure. In some embodiments, operation 312 is performed by a control module the same as or similar to control module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for providing respiratory therapy during a therapy session to a subject, the system comprising:
   a pressure generator configured to generate a pressurized flow of breathable gas for delivery to the airway of the subject, the pressure generator having an output configured to expel the pressurized flow of breathable gas;
   a subject interface configured to guide the pressurized flow of breathable gas from the output of the pressure generator to a point of delivery at or near the airway of the subject, wherein the subject interface causes a pressure drop between the output of the pressure generator and the point of delivery during delivery of the pressurized flow of breathable gas;
   one or more sensors configured to generate output signals conveying information related to one or more gas parameters of the pressurized flow of breathable gas at the point of delivery at or near the airway of the subject, wherein the output signals are generated in an ongoing manner during the therapy session, and wherein a first sensor of the one or more sensors is disposed at the point of delivery at or near the airway of the subject; and
   one or more processors configured to execute processing modules, the processing modules comprising:
   an estimation module configured to estimate the pressure drop between the output of the pressure generator and the point of delivery during delivery of the pressurized flow of breathable gas based on the generated output signals, wherein the estimation by the estimation module is performed in an ongoing manner during the therapy session;
   a target module configured to determine a target pressure for the pressurized flow of breathable gas that compensates for the dynamically estimated pressure drop, wherein the target pressure is in accordance with a therapy regimen;
   a control module configured to adjust levels of one or more gas parameters of the pressurized flow of breathable gas based on the determined target pressure; and
   a model module configured to adjust one or more model parameters of a parameter-based model that models the subject interface, the one or more model parameters being different than the one or more gas parameters, wherein the parameter-based model includes one or more model parameters related to pneumatic impedance of the subject interface, wherein adjustments of the one or more model parameters are performed in an ongoing manner based on the one or more gas parameters and/or the output signals during the therapy session, wherein the adjustments include correcting the one or more model parameters and/or adding one or more additional model parameters to the parameter-based model, and wherein the estimation by the estimation module is further based on the one or more adjusted model parameters of the parameter-based model.

2. The system of claim 1, further comprising:
   a subject interface appliance included in the subject interface, wherein the subject interface appliance is configured to deliver the pressurized flow of breathable gas to the airway of the subject, wherein the first sensor is disposed within the subject interface appliance,
   and wherein adjustments by the control module are further based on the parameter-based model.

3. The system of claim 1, wherein operation of the estimation module configured to estimate the pressure drop is further based on a device pressure estimation of a pressure at or near the output of the pressure generator, wherein the device pressure estimation is based on a measurement of a component of the pressure generator.

4. The system of claim 1, further comprising:
   a patient pressure module configured to determine a patient pressure at the point of delivery based on the generated output signals from the first sensor at the point of delivery;
   a device pressure module configured to estimate a device pressure at the output of the pressure generator; and
   an error module configured to determine a pressure error based on a difference between the target pressure and the estimated device pressure
   wherein the adjustments by the model module are further based on the patient pressure and the device pressure, and wherein adjustments by the control module are further based on the pressure error.

5. The system of claim 1, wherein the estimation module is configured to dynamically estimate the pressure drop due to flow changes caused by the subject.

6. A method for estimating a pressure drop during the provision of respiratory therapy to a subject, the method being implemented in a system including a pressure generator, a subject interface, and one or more sensors, the method comprising:

guiding a pressurized flow of breathable gas from an output of the pressure generator to a point of delivery at or near an airway of the subject via the subject interface, wherein the subject interface causes a pressure drop between the output of the pressure generator and the point of delivery during delivery of the pressurized flow of breathable gas;

generating, by a first sensor of the one or more sensors, output signals conveying information related to one or more gas parameters of the pressurized flow of breathable gas at the point of delivery at or near the airway of the subject, wherein the output signals are generated in an ongoing manner during the therapy session;

estimating the pressure drop between the output of the pressure generator and the point of delivery of the pressurized flow of breathable gas based on the generated output signals, wherein the estimation is performed dynamically in an ongoing manner during the therapy session;

determining, with a target module, a target pressure for the pressurized flow of breathable gas that compensates for the dynamically estimated pressure drop, wherein the target pressure is in accordance with a therapy regimen;

adjusting, with a control module, levels of one or more gas parameters of the pressurized flow of breathable gas based on the determined target pressure; and adjusting one or more model parameters of a parameter-based model that models the subject interface, the one or more model parameters being different than the one or more gas parameters, wherein the parameter-based model includes one or more model parameters related to pneumatic impedance of the subject interface, and wherein adjustments of the one or more model parameters are performed in an ongoing manner based on the one or more gas parameters and/or the output signals during the therapy session, wherein the adjustments include correcting the one or more model parameters and/or adding one or more additional model parameters to the parameter-based model, and wherein the estimation by the estimation module is further based on the one or more adjusted model parameters of the parameter-based model.

7. The method of claim 6, further wherein:
the subject interface appliance is configured to deliver the pressurized flow of breathable gas to the airway of the subject, wherein the first sensor is disposed within the subject interface appliance, and wherein adjustments by the control module are further based on the parameter-based model.

8. The method of claim 6, wherein estimating the pressure drop is based on a device pressure estimation of a pressure at or near the output of the pressure generator, wherein the device pressure estimation is based on a measurement of a component of the pressure generator.

9. The method of claim 6, further comprising:
generating, by a second sensor of the one or more sensors, output signals conveying information related to one or more gas parameters of the pressurized flow of breathable gas at the output of the pressure generator;
determining a patient pressure at the point of delivery based on the output signals generated by the first sensor;

estimating a device pressure at the output of the pressure generator based on the particular output signals generated by the second sensor; and determining a pressure error based on a difference between the determined target pressure and the determined device pressure,
wherein estimating the pressure drop is further based on the pressure error.

10. The method of claim 6, wherein estimating the pressure drop includes dynamically estimating the pressure drop due to flow changes caused by the subject.

11. A system configured providing respiratory therapy during a therapy session to a subject, the system comprising:

pressure means for generating a pressurized flow of breathable gas for delivery to the airway of the subject;

guiding means for guiding the pressurized flow of breathable gas from an output of the pressure means to a point of delivery at or near the airway of the subject, wherein the guiding means causes a pressure drop between the output of the pressure means and the point of delivery during delivery of the pressurized flow of breathable gas;

first means for generating output signals conveying information related to one or more gas parameters of the pressurized flow of breathable gas at the point of delivery at or near the airway of the subject, wherein the output signals are generated in an ongoing manner during the therapy session, and wherein the first means for generating output signals is disposed at the point of delivery at or near the airway of the subject;

means for estimating the pressure drop between the output of the pressure means and the point of delivery of the pressurized flow of breathable gas based on the generated output signals, wherein operation of the means for estimating is performed in an ongoing manner during the therapy session;

means for determining a target pressure for the pressurized flow of breathable gas configured to compensate for the estimated pressure drop, wherein the target pressure is in accordance with a therapy regimen;

means for adjusting levels of one or more gas parameters of the pressurized flow of breathable gas based on the determined target pressure; and means for adjusting, in an ongoing manner during the therapy session based on the output signals, one or more model parameters of a parameter-based model that models the guiding means, the one or more model parameters being different than the one or more gas parameters, wherein the parameter-based model includes one or more model parameters related to pneumatic impedance of the guiding means, wherein adjustments of the one or more model parameters are performed in an ongoing manner based on the one or more gas parameters and/or the output signals during the therapy session, wherein the adjustments include correcting the one or more model parameters and/or adding one or more additional model parameters to the parameter-based model, and wherein operation of the means for estimating the pressure drop is further based on the one or more adjusted model parameters of the parameter-based model.

12. The system of claim 11, further comprising:
means for delivering the pressurized flow of breathable gas to the airway of the subject, wherein the means for delivering is included in the guiding means, and wherein the first means for generating the output signals is disposed within the means for delivering, and wherein operation of the means for adjusting the levels of one or more gas parameters is further based on the parameter-based model.

13. The system of claim 11, wherein operation of the means for estimating the pressure drop is based on a device pressure estimation of a pressure at or near the output of the pressure generator, wherein the device pressure estimation is based on a measurement of a component of the pressure generator.

14. The system of claim 12, further comprising:
second means for generating output signals conveying information related to one or more gas parameters of the pressurized flow of breathable gas at the output of the pressure generator;
means for determining a patient pressure at the point of delivery based on the output signals generated by the first means;
means for estimating a device pressure at the output of the pressure generator based on the particular output signals generated by the second means; and
means for determining a pressure error based on a difference between the determined target pressure and the estimated device pressure,
wherein operation of the means for adjusting the one or more parameters of the parameter-based model is based on the patient pressure and the device pressure, and wherein operation of the means for adjusting the levels of one or more gas parameters is further based on the pressure error.

15. The system of claim 11, wherein the means for estimating the pressure drop is configured to dynamically estimate the pressure drop due to flow changes caused by the subject.

16. The system of claim 1, wherein the one or more model parameters related to pneumatic impedance of the subject interface comprise one or more of a hose resistance of a hose of the subject interface, a hose inertance of the hose, a resistance of a subject interface appliance of the subject interface, or a leak resistance of the subject interface.

17. The method of claim 6, wherein the one or more model parameters related to pneumatic impedance of the subject interface comprise one or more of a hose resistance of a hose of the subject interface, a hose inertance of the hose, a resistance of a subject interface appliance of the subject interface, or a leak resistance of the subject interface.

18. The system of claim 11, wherein the one or more model parameters related to pneumatic impedance of the subject interface comprise one or more of a hose resistance of a hose of the subject interface, a hose inertance of the hose, a resistance of a subject interface appliance of the subject interface, or a leak resistance of the subject interface.

* * * * *